(12) United States Patent
Davydov et al.

(10) Patent No.: US 9,772,308 B2
(45) Date of Patent: Sep. 26, 2017

(54) METHOD OF ELECTROMAGNETIC DEFECTOSCOPY FOR MULTI-STRING WELLS AND THE ELECTROMAGNETIC DOWNHOLE DEFECTOSCOPE

(71) Applicant: MIKS LLC, Kazan (RU)

(72) Inventors: Dmitry Aleksandrovich Davydov, Kazan (RU); Artur Mikhailovich Aslanian, Kazan (RU); Andrei Aleksandrovich Arbuzov, Kazan (RU); Dmitry Yuryevich Pyatnitsky, Saratov (RU)

(73) Assignee: MIKS LLC, Kazan (RU)

( * ) Notice: Subject to any disclaimer, the term of this patent is extended or adjusted under 35 U.S.C. 154(b) by 0 days.

(21) Appl. No.: 14/007,973

(22) PCT Filed: Dec. 3, 2012

(86) PCT No.: PCT/RU2012/001007
§ 371 (c)(1),
(2) Date: Sep. 27, 2013

(87) PCT Pub. No.: WO2014/035285
PCT Pub. Date: Mar. 6, 2014

(65) Prior Publication Data
US 2015/0219601 A1 Aug. 6, 2015

(30) Foreign Application Priority Data
Aug. 31, 2012 (RU) .................................. 2012137077

(51) Int. Cl.
*G01N 27/90* (2006.01)
*E21B 47/00* (2012.01)
(Continued)

(52) U.S. Cl.
CPC ............. *G01N 27/90* (2013.01); *E21B 47/00* (2013.01); *E21B 47/06* (2013.01); *E21B 47/065* (2013.01);
(Continued)

(58) Field of Classification Search
None
See application file for complete search history.

(56) References Cited

U.S. PATENT DOCUMENTS

| 5,532,591 A * | 7/1996 | Logue ................... B82Y 15/00 |
| | | 209/567 |
| 2007/0199696 A1* | 8/2007 | Walford .............. E21B 43/2406 |
| | | 166/250.01 |

(Continued)

FOREIGN PATENT DOCUMENTS

CN        201322740 Y    * 10/2009

OTHER PUBLICATIONS

Machine English Translation of CN201322740.*
(Continued)

*Primary Examiner* — Jermele M Hollington
*Assistant Examiner* — Douglas X Rodriguez
(74) *Attorney, Agent, or Firm* — Boyle Fredrickson S.C.

(57) ABSTRACT

This invention relates to the monitoring of the integrity of casing, tubing and other strings in oil and gas wells. The technical result of this invention consists in increased accuracy and trustworthiness in detecting and locating transverse and longitudinal defects in well completion components and downhole equipment, in both the magnetic and non-magnetic first, second and other metal barriers. Electromagnetic defectoscopy in multi-string wells includes measuring EMF induced in a coil by eddy currents generated in metal barriers by the decay of the electromagnetic field produced by magnetization current pulses in the coil. A series of pulses of (Continued)

fixed duration in the range of 0.1-1000 ms is fed to each exciter-and-pickup coil to sequentially magnetize all metal barriers starting from the nearest one, with pulse durations increasing for each next barrier. The recorded data are saved and processed by comparing them with model data, and the processing results indicate detects in the metal barriers. The downhole electromagnetic defectoscope contains a case, axially oriented coils with their magnetic axes coinciding with the tool's magnetic axis, and an electronic module, and at least two exciter-and-pickup coils, each consisting of an exciter coil and a pickup coil with a single core. The exciter-and-pickup coils are of different sizes and are spaced apart by a distance of not less than the length of the larger exciter-and-pickup coil.

38 Claims, 5 Drawing Sheets

(51) Int. Cl.
  *E21B 47/06* (2012.01)
  *E21B 47/12* (2012.01)
  *E21B 49/00* (2006.01)
  *G01B 7/06* (2006.01)
  *G01N 17/00* (2006.01)

(52) U.S. Cl.
  CPC ............ *E21B 47/12* (2013.01); *E21B 49/003* (2013.01); *G01B 7/10* (2013.01); *G01N 17/006* (2013.01); *G01N 27/902* (2013.01)

(56) References Cited

U.S. PATENT DOCUMENTS

| | | | |
|---|---|---|---|
| 2009/0166035 A1* | 7/2009 | Almaguer | E21B 7/061 166/254.1 |
| 2010/0207711 A1* | 8/2010 | Estes | E21B 47/082 333/24 C |
| 2011/0163740 A1* | 7/2011 | Russell | G01N 27/72 324/220 |
| 2012/0095686 A1* | 4/2012 | Legendre | E21B 47/082 702/6 |

OTHER PUBLICATIONS

Brill et al., "Electromagnetic Casing Inspection Tool for Corrosion Evaluation", International Petroleum Technology Conference, Bangkok; Thailand, Feb. 7-9, 2012.
Brill et al., "Quantitative Corrosion Assessment with an EM Casing Inspection Tool", SPE/DGS Saudi Arabia Section Technical Symposiums and Exhibition, May 15-18, 2011.
Rourke et al., "Multi-Tubular Corrosion Inspection Using a Pulsed Eddy Current Logging Tool", International Petroleum Technology Conference, Beijing, China, Mar. 26-28, 2013.
Arbuzcv et al., "Memory Magnetic Imaging Defectoscopy", SPE Russian Oil & Gas Exploration & Production Technical Conference and Exhibition. Moscow, Russia. Oct. 16-18, 2012.
Ansari et al., "Triple-Barrier Thickness Scanning Using Through-Tubing Pulse-Magnetic Logging Tool", SPE Russian Petroleum Technology Conference, Moscow, Russia, Oct. 26-28, 2015.

* cited by examiner

METHOD OF ELECTROMAGNETIC DEFECTOSCOPY FOR MULTI-STRING WELLS AND THE ELECTROMAGNETIC DOWNHOLE DEFECTOSCOPE

This invention relates to the monitoring of the integrity of casing, tubing and other strings in oil and gas wells.

There is a known method of electromagnetic defectoscopy for multi-string wells (Russian Federation Patent No 2364719, IPC E21B47/08, G01N27/90, published 20 Aug. 2009) that is closest in its technical essence to the claimed invention and is taken as a prototype consists in measuring EMF induced in a pickup coil by eddy currents generated in steel pipes by electromagnetic field decay caused by transmitted pulses of magnetizing currents of varying duration in an exciter coil.

The drawback of this method is the use of single-detector defectoscope, which does not allow reliable differentiation between responses from the first and second metal barriers of different diameters: if the length of the long detector is equal to the diameter of the second metal barrier, the detected response inevitably depends on the characteristics of the second barrier even for short pulses generated, and if the length of the short detector is equal to the diameter of the first metal barrier, the detected response mainly depends on the characteristics of the first metal barrier even for long pulses generated, while the influence of the second metal barrier would be small.

This method also does not allow the analysis of non-magnetic stainless-steel pipes, because the narrow 10-40-ms range of short pulses, or the analysis of more than two barriers because of the limited 40-200-ms range of long pulses. The claimed method allows the analysis of two or more metal barriers including non-magnetic stainless-steel pipes using short 0.1-10-ms pulses and the analysis of the third, fourth and other barriers due to the wide 0.1-1000-ms range of long pulses. There is a known downhole electromagnetic defectoscope that employs two longitudinal detectors of different lengths to more reliably differentiate between internal and external columns (Teplukhin. V. K. et al. Improvement in Equipment and Technology of Downhole Electromagnetic Defectoscopy. The Well Logger Science and Technology Bulletin, Tver, AIS, 2006, issue 149, 173-183; Teplukhin, V. K., Miller, A. V. and Sidorov, V. A. Multi-Detector Digital Electromagnetic Thickness-Gauging Defectoscope. New Well-Logging Equipment for Drilled and Operating Vertical, Slanted and Horizontal Wells. Abstracts of the Ufa International Symposium, 23-24 Apr. 1997, 29-30. In Russian).

The drawback of this device is the use of pulses of equal durations for both detectors, which does not allow the reliable characterisation of the first and second metal barriers: if pulses are short, the recorded response of the long detector mainly depends on the parameters of the first metal barrier while the influence of the second metal barrier is small; if pulses are long, the recorded response of the short detector inevitably depends on the parameters of the second barrier.

These is a known downhole electromagnetic defectoscope (Russian Federation Patent No. 2372478, IPC E21B47/00, published 10 Nov. 2009) consisting of a case, an electronic module, an exciter inductance coil and not less than three peripherally located pick-up inductance coils with magnetic axes perpendicular to the tool axis.

The drawback of this device is the use of one exciter coil of fixed length and pulses of fixed duration, which enables the analysis of the first metal barrier only. Moreover, the separation of the exciter and pick-up coils in space results in double recording of anomalies produced by one defect.

There is a known downhole electromagnetic defectoscope (Patent No. 2215143, IPC E21B49/00, G01N27/90, published 27 Oct. 2003) consisting of a case, an exciter coil, differentially connected pick-up coils located at some distance from the exciter coil along the tool axis, an electronic module and more than one pair of pick-up coils forced against the borehole wall. The exciter coil is a solenoid with a length of more than two diameters of the survey well and with the magnetic axes of the pick-up coils being perpendicular to the tool axis.

There is a known downhole magnetic-pulse thickness-gauging defectoscope (Russian Federation Patent No. 2333461, IPC G01B7/02, E21B47/12, published 10 Sep. 2008) that is closest in technical essence to the claimed invention and taken as a prototype, consisting of a generator system with a generator, a timer and exciter inductance coils, a measuring system with measuring inductance coils, and additional inductance coils located far from the exciter coil.

The drawback of this device is the separation of the exciter and pick-up coils in space, which results in double recording of anomalies produced by one defect. The use of a telemetry line requires the use of a logging cable. When transmitted through a logging cable, information can be distorted by noise or varying wellbore temperature. The use of cabled devices also significantly increases the cost of survey. Application of additional inductance coils substantially increases the length of the device.

In known devices, the exciter and pickup coils are spaced apart, each producing an anomaly when passing by a defect.

The proposed technical solution is to avoid the aforementioned disadvantages and ensure high-precision and high-quality defectoscopy and thickness measurements in strings of various diameters through reliable separation of responses from each barrier.

The claimed device avoids doubling the aforementioned response anomaly produced by a single defect due to the integration of the exciter and pickup coils into one exciter-and-pickup coil with a single core.

The proposed downhole electromagnetic defectoscope (hereinafter referred to as "the defectoscope") is designed to detect defects and measure wall thickness simultaneously in tubing ("the first metal barrier"), production casing ("the second metal barrier") and other strings (the third, fourth, etc. barriers) of the well. The defectoscope can detect and locate transverse and longitudinal defects (both internal and external) and well completion components, check perforation quality and downhole equipment condition, and determine the deviation of the wall thickness from its nominal value through the interpretation of defectoscopy data. Pipes may be made of various steel and corrosion resistant alloys including non-magnetic ones. The claimed method and device allow determining the deviation of the pipe wall thickness from its nominal value. The claimed method and device also allow the analysis of non-magnetic metal pipes and differentiation between internal and external corrosions and between through and blind perforations by recording responses from an early time of ca. 0.1 ms thanks to the use of a core with a characteristic transient decay time of less than 0.1 ms.

The technical result of this invention is increased accuracy and trustworthiness in detecting and locating transverse and longitudinal defects in well completion components and downhole equipment, in both the magnetic and non-magnetic first, second and other metal barriers. The novelty in the electromagnetic defectoscopy—conducted in multi-string wells by measuring EMF induced in a coil by eddy currents generated in metal barriers by the decay of the electromagnetic field in turn produced by magnetization current pulses in the coil—allowing this technical result to be achieved is that a series of pulses of fixed duration in the range of 0.1-1000 ms is fed to each of the exciter-and-pickup coils to sequentially magnetize all metal barriers starting from the nearest one with pulse durations increasing for each next barrier; the recorded data ore saved and processed by comparing them with model data, and the processing results indicate defects in the metal barriers.

The whole measurement cycle is continuously repeated at various depths when moving across the zone of interest.

Defects can be represented by through and blind perforations and external, internal and through corrosion.

The first magnetization current pulse is 0.1-100 ms long and the second one is 0.1-800 ms long.

The first response, that is a self-induced EMF decay in time, is recorded during 0.1-150 ms following the end of the first pulse.

The second response, also a self-induced EMF decay in time, is recorded during 0.1-1000 ms after the end of the second pulse.

The processing of the obtained data consists in comparing each recorded response with a set of model responses to find a matching one, its parameters being the metal barrier parameters to be determined (wall thickness, diameter, magnetic permeability and electrical conductivity).

A decrease in wall thickness of more than 12 percent indicates a defect in the metal barrier.

In each measurement cycle, a measurement of the last response is additionally followed by measurements of ambient temperature and pressure.

The temperature-depth and pressure-depth functions are built, and through defects are detected by analysing changes in temperature and/or pressure gradient(s).

Defects are detected by analysing responses at early times of 0.1-10 ms.

Through defects are detected by analysing responses throughout the recording interval of 0.1-1000 ms.

The time of running-in to the zone of interest, the measurement time depending on the length of the zone of interest and tool speed in it, the magnetization current pulse duration and the current amplitude for exciter-and-pickup coils are set prior to measurements.

The duration of the first pulse is set in such a way that the skin depth for the first harmonic of its Fourier spectrum is approximately equal to the nominal thickness of the first metal barrier.

The duration of the second pulse is set in such a way that the skin depth for the first harmonic of its Fourier spectrum is approximately equal to the sum of nominal thicknesses of the first and second metal barriers.

The durations of subsequent pulses are set in such a way that the skin depth for the first harmonic of their Fourier spectrum is approximately equal to the sum of nominal thicknesses of the first, second and other metal barriers.

Model responses are generated taking into account the preliminarily measured remanent magnetization of metal barriers to increase the accuracy of their characterisation.

Measurements are made in vertical wells while running in or pulling out of hole and in deviated wells while pulling out.

Measurements are made at a constant tool speed of 1-30 m/min.

The technical result is achieved through the novelty consisting in the fact that the downhole electromagnetic defectoscope—containing a case, axially oriented coils with their magnetic axes coinciding with the tool's magnetic axis, and an electronic module—contains at least two exciter-and-pickup coils of different sizes, each consisting of an exciter coil and a pickup coil with a single core, that are spaced apart by a distance of not less than the length of the large exciter-and-pickup coil.

The tool additionally contains pressure, temperature and magnetic field sensors.

The electronic module can generate independent pulses of fixed duration in the range of 0.1-1000 ms is fed to the large, small and other exciter-and-pickup coils, and can record and save their responses.

The electronic module includes a memory unit.

The electronic module also contains a signal amplifier.

The length of the small exciter-and-pickup coil is approximately 4/3 of the diameter of the first metal barrier, the length of the large exciter-and-pickup coil is approximately 4/3 of the diameter of the second metal barrier, and the length of each next coil is approximately 4/3 of the diameter of each next metal barrier.

The first metal barrier can be tubing and the second one can be production casing. The other metal barriers can be conductor pipe and surface casing.

The number of exciter-and-pickup coils is equal to the number of metal barriers under study.

The small exciter-and-pickup coil can be placed above the large one.

The distance between the small and large exciter-and-pickup coils does not exceed the tool length.

The small and large exciter-and-pickup coils contain exciter winding wound around pickup winding that is, in turn, wound around cores.

The electronic module and magnetic field sensor are located between the small and large exciter-and-pickup coils.

The temperature and pressure sensors can be located in the lower part of the tool, under the large exciter-and-pickup coil.

The small and large exciter-and-pickup coils and magnetic field, pressure and temperature sensors are connected to the electronic module.

The tool has a battery compartment that can be located in its upper part and is connected to the electronic module.

The upper and lower centralizers are installed at the top and bottom of the tool, respectively.

The cores of the exciter-and-pickup coils can be made of soft ferromagnetic material with a relaxation time of less than 0.1 ms.

The case can be mode of titanium.

The essence of the invention is illustrated in figures.

Figure 1:
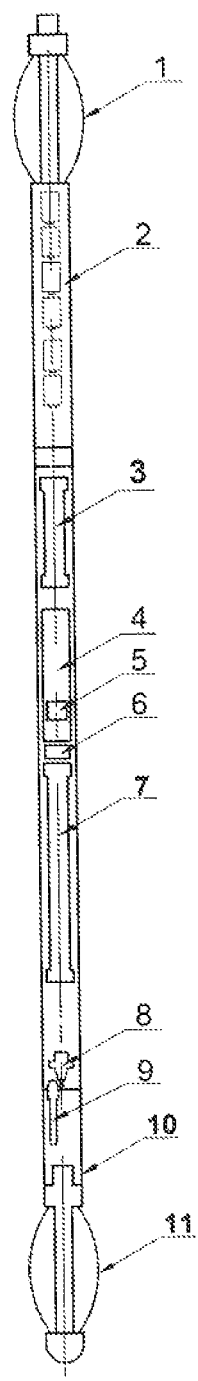
FIG. 1 is a schematic diagram of the downhole electromagnetic defectoscope.
Figure 2:
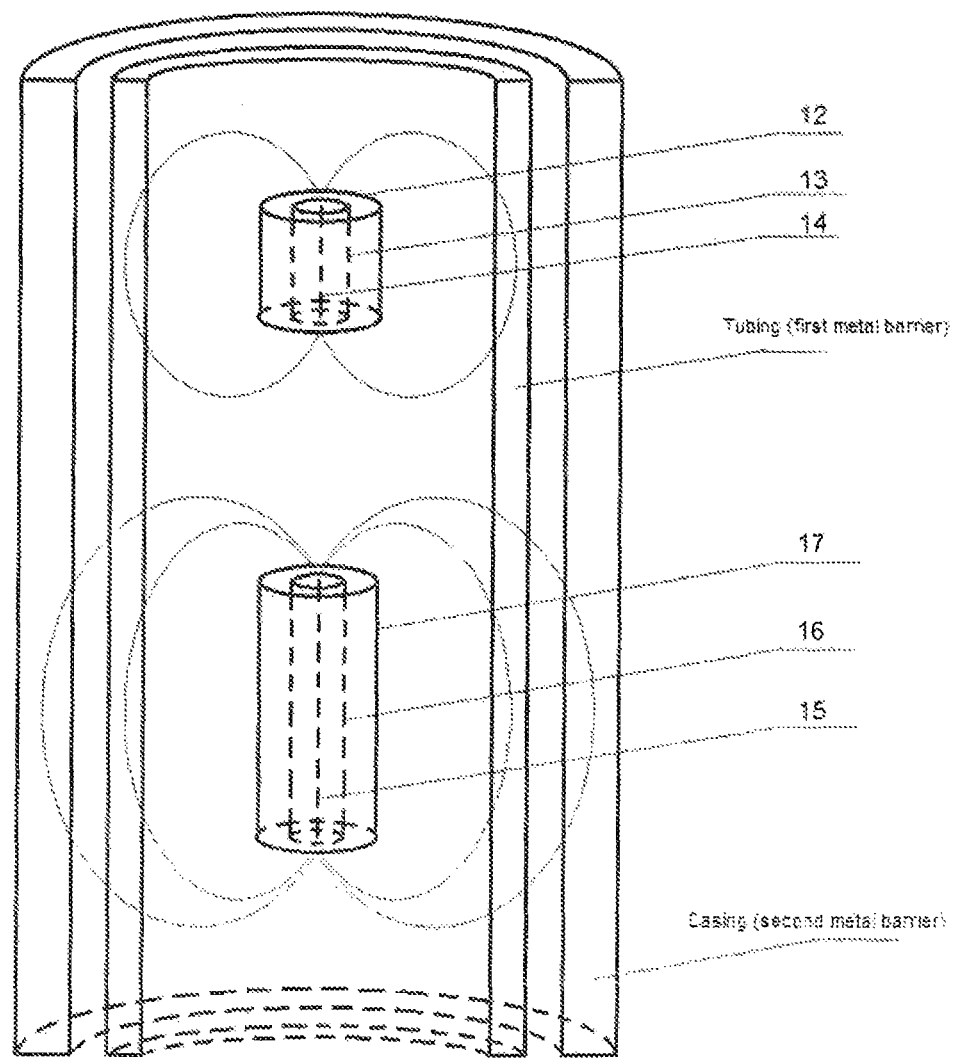
FIG. 2 illustrates the separation of the responses of two metal barriers when using two exciter-and-pickup coils.

The essence of the method is as follows.

Measurements are made in vertical wells while running in or pulling out of hole and in deviated wells while pulling out.

The time of running-in to the zone of interest, the toot running time through the zone of interest depending on its length, the duration of the first (short), second (long) and other pulses and the current amplitudes for the small, large and other exciter-and-pickup coils are set prior to measurements.

The duration of the first pulse is set in such a way that the skin depth for the first harmonic of its Fourier spectrum is approximately equal to the wall thickness of the first metal barrier.

The duration of the second pulse is set in such a way that the skin depth for the first harmonic of its Fourier spectrum is approximately equal to the sum of wall thicknesses of the first and second metal barriers. The durations of subsequent pulses are set in such a way that the skin depth for the first harmonic of their Fourier spectra is approximately equal to the sum of the wall thicknesses of the first, second and other metal barriers.

Magnetic field intensity, i.e. remanent magnetization of pipes, is measured at the start of a measurement cycle, before magnetizing the metal barriers under study.

The first, low-amplitude, magnetization current pulse of 0.1-100 ms duration is fed to the exciter winding of the small exciter-and-pickup coil. The electromagnetic field created by the small exciter-and-pickup coil magnetizes the first metal bonier.

The first response, that is a self-induced EMF, is recorded during 0.1-150 ms following the end of the first pulse and is then saved.

Then, the second, high-amplitude, magnetization current pulse of 0.1-800 ms duration is fed to the exciter winding of the large exciter-and-pickup coil. The electromagnetic field created by the large exciter-and-pickup coil magnetizes the first and second metal barriers.

The second response, that is a self-induced EMF, is recorded during 0.1-1000 ms following the end of the second pulse and is then saved.

Depending on the number of barriers under study, subsequent pulses are fed and their corresponding responses are measured in the same way, and EMF decay in time at certain depths is thus recorded.

A measurement of the last response is followed by measurements of ambient temperature and pressure at a certain depth.

The measurement cycle is repeated continuously at various depths while the tool is running through the zone of interest, that is the whole well in the general case. After the measurements, the collected data are processed.

The processing results are used to determine the parameters of metal barriers, i.e. magnetic permeability, electrical conductivity, pipe wall thicknesses and diameters, that are in turn used to detect defects, through and blind perforations, and external and internal corrosion.

The parameters of metal barriers are determined by modelling their responses, i.e. model EMF decays in time for magnetic permeability, electrical conductivity, thickness and diameter (see Dmitriev. V. I., 1972, Axisymmetric Electromagnetic Field in a Cylindrical Layered Medium. Physics of the Earth. No. 11, In Russian). Each parameter of a barrier varies within a certain range.

The barrier wall thickness varies between 0.1 mm and its double nominal thickness at 0.1-mm intervals. The diameter of a barrier varies from 43 mm to 508 mm at 0.1-mm intervals. (The nominal wall thickness of a barrier and its diameter are known from a well data sheet.)

The magnetic permeability of a barrier varies from 1 to 5000 at 0.1 intervals. The electrical conductivity of a barrier is modelled between 105 S/m and 108 S/m at 105-S/m intervals (Kuchling, H. Handbook of Physics [Russian translation], Mir, Moscow, 1982).

The modelling takes into account the measured remanent magnetization of a barrier, which increases the accuracy of its characterisation.

Each recorded response is superimposed on the model responses to find a matching one. The parameters of such a model response are the ones to be determined for a metal barrier (wall thickness, diameter, electrical conductivity and relative magnetic permeability).

In order to detect and locate defects in metal barriers, the determined wall thickness is compared with the nominal one given in the well data sheet.

A deviation of the wall thickness from its nominal value of more than 12 percent indicates a well defect.

The defect is located using the known tool speed, length of the zone of interest and measurement time.

The next step is to determine whether the defect is a through one
by analysing the obtained dependences of temperature and pressure on depth.

If there are no through defects and the fluid type does not change, temperature and pressure increase with depth with a constant gradient.

The depth of a through defect is determined by the change in temperature and/or pressure gradients.

Analysis of input defectoscope data allows the differentiation of internal defects (corrosion) in the first and second metal barriers from external ones.

Figure 3:
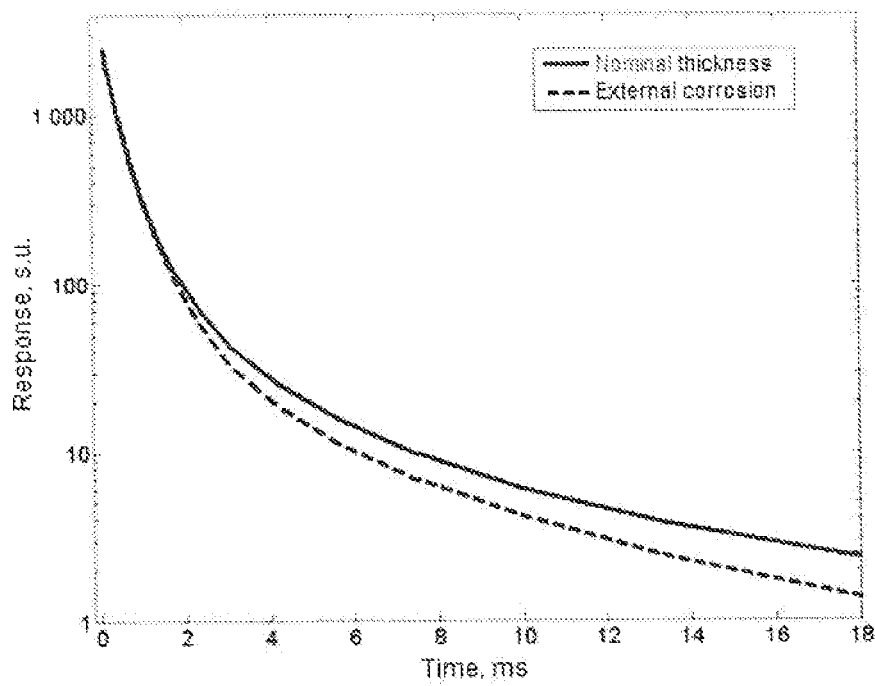
FIG. 3 shows the responses of an intact portion of the pipe (nominal response) and a section containing external corrosion.
Figure 4:
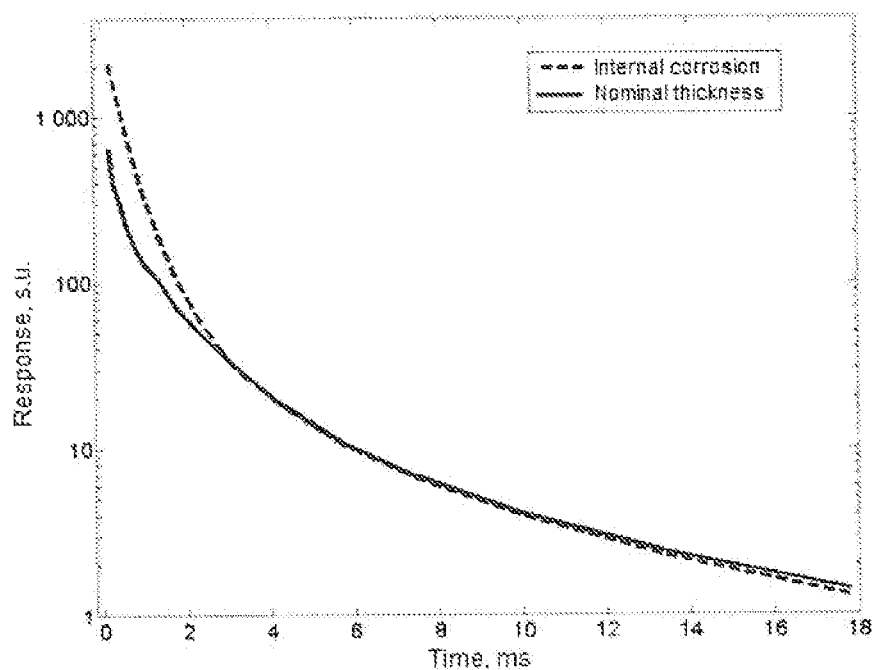
FIG. 4 shows the responses of an intact portion of the pipe (nominal response) and a section containing internal corrosion.
Figure 5:
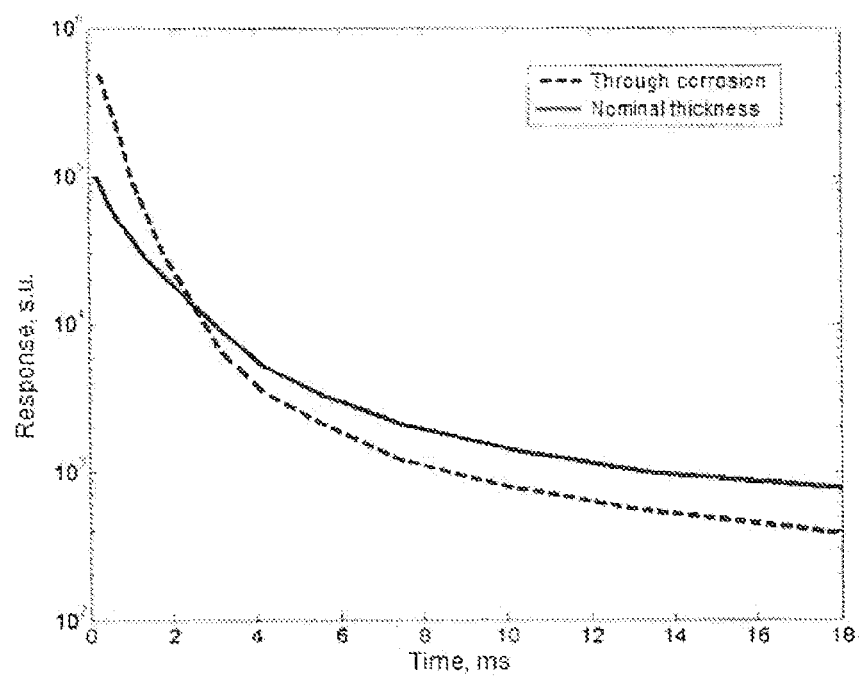
FIG. 5 shows the responses of an intact portion of the pipe (nominal response) and a section containing through corrosion.

Also, through perforations in the first or second metal carrier can be differentiated from blind ones. The differences between responses from blind perforations or internal corrosion and nominal responses are mainly observed at early times of 0.1-10 ms (FIG. 4), while the differences between responses from through perforations and nominal responses are observed at both early and late times (FIG. 5). The difference between the external corrosion response and nominal one show at late times of 10-1000 ms (FIG. 3).

The corrosion response has a larger amplitude at early times and a lower one at late times. The smaller amount of metal makes the signal change faster: the corrosion signal rapidly increases at early times of 0.1-10 ms and then rapidly decreases at 0.1-1000 ms times.

Figure 6:
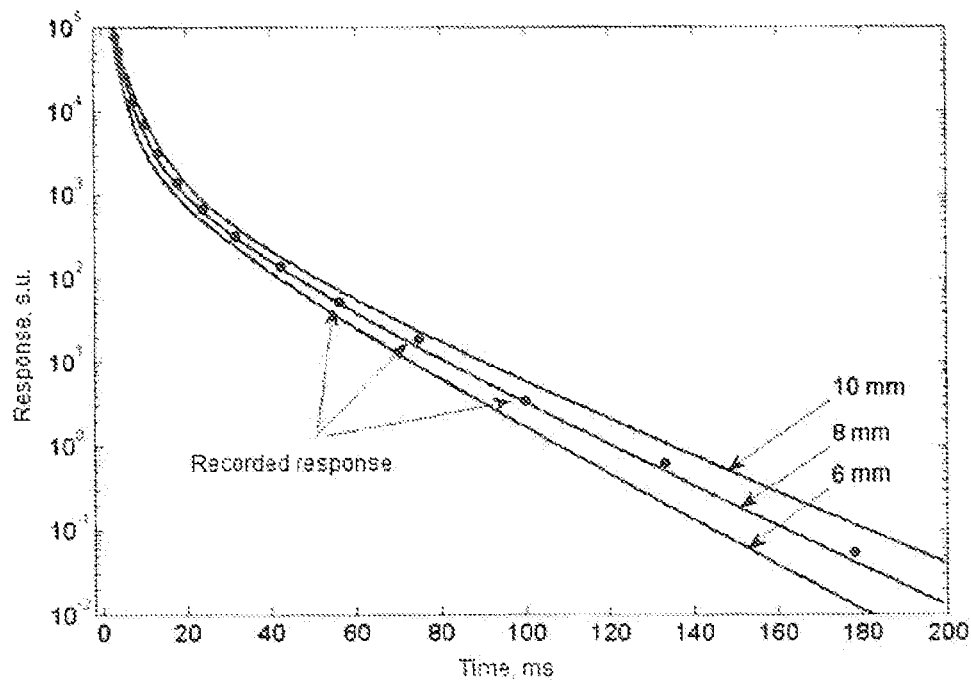
FIG. 6 shows the responses of two metal barriers and model signal decays calculated for various tubing wall thicknesses.
Figure 7:
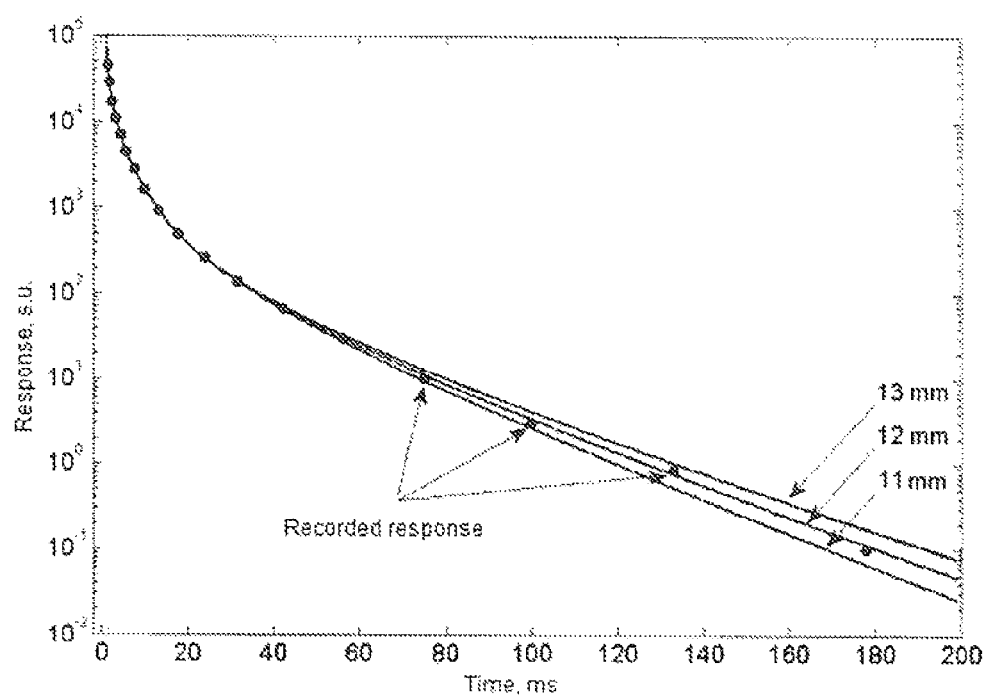
FIG. 7 shows the responses of two metal barriers and model signal decays calculated for various casing wall thicknesses.

FIGS. 6 and 7 show how pipe wall thickness affects the model response (EMF decay in time) while varying the thicknesses of an internal barrier (tubing in FIG. 6) and an external bonier (casing in FIG. 7). Changes in the thickness of an infernal barrier affect the whole signal, while changes in the thickness of an external barrier show only at late times. The recording of responses at 0.1-10 ms enables the analysis of pipes made of various steel and corrosion-resistant alloys including non-magnetic; responses from non-magnetic pipes are ca. 10-ms long and cannot be detected by known electromagnetic defectoscopes, while responses from magnetic pipes are ca. 50-250-ms long.

The device that allows the implementation of the method consists of the following components:

1—Upper Centralizer; 2—Battery Compartment; 3 Small Exciter-and-Pickup Coil; 4—Electronic Module;

5—Memory Unit; 6—Magnetic Field Sensor; 7—Large Exciter-and-Pickup Coil; 8—Pressure Sensor; 9—Temperature Sensor; 10—Case; 11—Lower Centralizer, 12—Exciter Winding of the Small Exciter-and-Pickup Coil; 13—Pickup Winding of the Small Exciter-and-Pickup Coil; 14—Core of the Small Exciter-and-Pickup Coil; 15—Core of the Large Exciter-rind-Pickup Coil; 16—Pickup Winding of the Large Exciter-and-Pickup Coil; 17—Exciter Winding of the Large Exciter-and-Pickup Coil.

The upper portion of Case 10 contains Battery Compartment 2; below that is a compartment containing Small Exciter-and-Pickup Coil 3 and Large Exciter-and-Pickup Coil 7 installed sequentially and longitudinally to the defectoscope's axis; and between them are Electronic Module 4 and Magnetic Field Sensor 6. Memory Unit 5 is contained in Electronic Module 4.

Electronic Module 4 also contains a signal amplifier.

Pressure Sensor 8 and Temperature Sensor 9 are in the lower portion of the device.

Battery Compartment 2, Small Exciter-and-Pickup Coil 3, Large Exciter-and-Pickup Coil 7, Magnetic Field Sensor 6, Pressure Sensor 8 and Temperature Sensor 9 are connected to Electronic Module 4.

Small Exciter-and-Pickup Coil 3 contains Pickup Winding 13 wound around Core 14 and Exciter Winding 12 wound around Pickup Winding 13. Large Exciter-and-Pickup Coil 7 contains Pickup Winding 16 wound around Core 15 and Exciter Winding 17 wound around Pickup Winding 16.

The length of Small Exciter-and-Pickup Coil 3 is approximately 4/3 of the diameter of tubing, that is the first metal barrier.

The length of Large Exciter-and-Pickup Coil 7 is approximately 4/3 of the diameter of casing, that is the second metal barrier.

The number of exciter-and-pickup coils is equal to the number of metal barriers under study, and the length of each exciter-and-pickup coil is 4/3 of the diameter of the corresponding metal barrier under stud.

Upper Centralizer 1 and Lower Centralizer 11 are installed at the top and bottom of the case, respectively.

The defectoscope is a stand-alone device powered by batteries installed in Battery Compartment 2.

The use of special core material—for instance, soft ferromagnetic material—with a characteristic transient decay time of less than 0.1 ms extends the observation time span at early times.

The corrosion-resistant material of Case 10—for instance, titanium—allows operation at high contents of hydrogen sulphide (up to 30%) and carbon dioxide.

Additional centralizers 1 and 11 enable centralizing the device within metal barriers under study and thus, increase data quality by preventing transverse vibrations of the defectoscope while it moves in the pipes.

The device operates as follows.

Before running the defectoscope into a well, it is programmed by setting a pre-operation delay (time of running to a zone of interest or to the maximum depth), operating time (time of travelling through a zone of interest), duration of pulses and current amplitudes for the small and large exciter-and-pickup coils. Measurements can be performed with the defectoscope in vertical wells while running in or pulling out of the hole and in deviated wells while pulling out because the speed of the defectoscope in deviated wells is more even while pulling out than while running in, as the fool can catch on the collars or other structural components of the first metal barrier.

The defectoscope is run in a well comprising one or more metal barriers—tubing, casing, surface casing, etc.—to the zone of interest or to the maximum depth, if the zone of interest is the entire well. The defectoscope moves along the well being centralized by Centralizers 1 and 11 connected to Case 10, The defectoscope operates in cycles, repeating a sequence of operations during the operating period that is set at the surface and depends on the time of passing the zone of interest and its length.

Detectoscop's Operation Cycle

At the start of a cycle, Magnetic Field Sensor 6 measures magnetic field intensity, before the magnetization by Coils 3 and 7, that is the remanent magnetization of the pipes. Electronic Module 4 powered from Battery Compartment 2 records the signal from Magnetic Field Sensor 6 and saves it to Memory Unit 5. Next, Electronic Module 4 sends the first, low-amplitude, magnetization current pulse of 0.1-100 ms duration to Exciter Winding of Small Exciter-and-Pickup Coil 12. Electromagnetic field generated by Small Exciter-and-Pickup Coil 3 with Core 14, with a length of 4/3 of the diameter of the first metal barrier under study, mainly magnetizes this barrier. Immediately after the end of the first pulse, self-induced EMF (the first response) appears in Pickup Winding of Exciter-and-Pickup Coil 13 according to Faraday's law and is recorded for 0.1-150 ms by Electronic Module 4 that saves the data to Memory Unit 5. This response determines the parameters of the first metal barrier. After recording the first response by Small Exciter-and-Pickup Coil 3, Electronic Module 4 feeds the second, high-amplitude, magnetization current pulse of 0.1-800 ms duration to Exciter Winding of Large Exciter-and-Pickup Coil 17. The electromagnetic field generated by Exciter-and-Pickup Coil 7, the length of which is approximately 4/3 of the diameter of the second metal barrier, magnetizes the first and second metal barriers. Immediately after the end of the second pulse, self-induced EMF the second response) appears in Pickup Winding of Exciter-and-Pickup Coil 16 according to Faraday's law and is recorded for 0.1-1000 ms by Electronic Module 4 that saves the data to Memory Unit 5.

After recording the second response of the Large Exciter-and-Pickup Coil 7, the temperature and pressure sensors 8 and 9 measure the temperature and pressure of their environment. Electronic Module 4 records signals from the pressure and temperature sensors 8 and 9 and saves them to Memory Unit 5. At this point, the defectoscope's operation cycle ends.

Then, the entire operation cycle is repeated for a period defined at the surface.

In all measurement cycles, the defectoscope continuously moves along the wellbore through a zone of interest at a speed of 1-30 m/min.

After surveying an entire zone of interest, the defectoscope is retrieved to the surface and connected to a computer that then receives the data accumulated in Memory Unit 5 and processes them in accordance with the claimed method.

The simultaneous use of at least two coils of different lengths and pulses of different durations in the defectoscope enables more accurate simultaneous measurements of wall thicknesses and assessments of defects in strings of various sizes. Short, low-amplitude pulses—with their durations set in such a way that the skin depth for the first harmonic is equal to the tubing wall thickness—fed to Exciter-and-Pickup Coil 3 allow it to scan only the first metal barrier.

Analysis of the first response of Small Exciter-and-Pickup Coil 3 enables the calculation of the thickness of the first barrier and location of its external and internal defects.

Long, high-amplitude pulses fed to Exciter-and-Pickup Coil 7 enable it to record the total response of the first and second metal barriers. Further processing of data from Large Exciter-and-Pickup Coil 7 allows the subtraction of the effect produced by the first metal barrier, the parameters of which are determined by processing data from Small Exciter-and-Pickup Coil 3, and the determination of the thickness and identification of defects of the second metal barrier.

Thus, analysis of data from at least two coils of different lengths enables the determination of the thicknesses of the first, second and other metal barriers and the identification of their defects.

The invention claimed is:

1. A method for electromagnetic defectoscopy conducted in multi-string wells comprising:
   measuring Electromagnetic Fields (EMF's) induced in pick-up coils by eddy currents generated in a plurality of metal barriers produced by magnetization current pulses in exciter coils, wherein the EMF's are induced in the pick-up coils by:
   (a) feeding a first magnetization current pulse having a first duration and a first amplitude to a first exciter coil for magnetizing a first metal barrier of the plurality of metal barriers; and
   (b) after step (a), feeding a second magnetization current pulse having a second duration and a second amplitude to a second exciter coil for magnetizing the first metal barrier of the plurality of metal barriers and a second metal barrier of the plurality of metal barriers,
   wherein the first duration is less than the second duration, the first amplitude is less than the second amplitude, the first and second durations are in a range from about 0.1 ms to about 1000 ms, and the first metal barrier is a nearest one of the plurality of metal barriers;
   storing the measured EMF as recorded data;
   processing said recorded data by comparing with model data; and
   identifying a defect in said metal barriers based on results of said processing.

2. The method of claim 1, further comprising continuously repeating said measuring, storing, processing and identifying steps while moving across a zone of interest.

3. The method of claim 1, wherein said defect includes a through perforation, a blind perforation, an external corrosion, an internal corrosion, or a through corrosion.

4. The method of claim 1, wherein the first duration is from about 0.1 ms to about 100 ms and the second duration is from about 0.1 ms to about 800 ms.

5. The method of claim 1, wherein said recorded data comprises a first response comprising a self-induced EMF decay in time, recorded following an end of the first magnetization current pulse, for a period of about 0.1 ms to about 150 ms in duration.

6. The method of claim 1, wherein said recorded data comprises a second response comprising a self-induced EMF decay in time, recorded following an end of the second magnetization current pulse, for a period of about 0.1 ms to about 1000 ms in duration.

7. The method of claim 1, wherein said processing comprises comparing each recorded response, comprised in said recorded data, with a set of model responses to identify a matching model response, wherein said each recorded response comprises parameters of a metal barrier, including a wall thickness, a diameter, a magnetic permeability, or an electrical conductivity.

8. The method of claim 7, wherein a decrease in said wall thickness of more than 12 percent indicates a defect in said metal barrier.

9. The method of claim 7, wherein model responses are generated taking into account a preliminarily measured remanent magnetization of said metal barriers.

10. The method of claim 1, further comprising measuring of an ambient temperature or pressure.

11. The method of claim 10, further comprising:
   constructing a temperature-depth function or a pressure-depth function;
   analyzing changes in temperature gradients or pressure gradients; and
   detecting through defects.

12. The method of claim 1, wherein said processing is conducted for a period from about 0.1 ms to about 10 ms in duration.

13. The method of claim 1, wherein said processing is conducted for a period from about 0.1 ms to about 1000 ms in duration and said defect is a through defect.

14. The method of claim 1, further comprising, prior to said measuring, setting a time of running-in to a zone of interest, a duration of said measuring depending on a length of said zone of interest and a tool speed in said zone of interest, a magnetization current pulse duration, or a current amplitude for exciter-and-pickup coils.

15. The method of claim 14, wherein the first pulse duration is set in such a way that a skin depth for a first harmonic of its Fourier spectrum is approximately equal to a nominal thickness of the first metal barrier.

16. The method of claim 14, wherein the second pulse duration is set in such a way that a skin depth for a first harmonic of its Fourier spectrum is approximately equal to a sum of nominal thicknesses of the first and second metal barriers.

17. The method of 14, wherein durations of successive pulses are set in such a way that skin depths for first harmonics of their Fourier spectra approximately equal to a sum of nominal thicknesses of successive metal barriers.

18. The method of claim 1, wherein said measuring is performed in vertical wells while running in or pulling out of a hole, and in deviated wells while pulling out.

19. The method of claim 1, wherein said measuring is performed at a constant tool speed of about 1 m/min to about 30 m/min.

20. A downhole electromagnetic defectoscope comprising:
   a case;
   a plurality of axially oriented coils, each having magnetic axis substantially coinciding with a longitudinal axis of the case; and
   an electronic module,
   wherein said coils comprise at least two exciter-and-pickup coils of different sizes, each exciter-and-pickup coil including an exciter coil and a pickup coil with a single core, wherein said coils are spaced apart by a distance of not less than a length of a larger exciter-and-pickup coil of the at least two exciter-and-pickup coils, and
   wherein said electronic module is configured to send a first magnetization current pulse having a first duration and a first amplitude to the exciter coil of a first exciter-and-pickup coil of said coils for magnetizing a first metal barrier of a plurality of metal barriers, and after sending the first magnetization current pulse, sending a second magnetization current pulse having a second duration and a second amplitude to the exciter coil of a second exciter-and-pickup coil of said coils for magnetizing the first metal barrier of the plurality of metal barriers and a second metal barrier of the plurality of metal barriers, wherein the first duration is less than the second duration, the first amplitude is less than the second amplitude, the first and second durations are in a range from about 0.1 ms to about 1000 ms, and the first metal barrier is nearest one of the plurality of metal barriers.

21. The defectoscope of claim 20, further comprising:
a pressure sensor;
a temperature sensor; and
a magnetic field sensor.

22. The defectoscope of claim 21, further comprising a smaller exciter-and-pickup coil of the at least two exciter-and-pickup coils, wherein said electronic module and said magnetic field sensor are located between said smaller and larger exciter-and-pickup coils.

23. A The defectoscope of claim 21, further comprising a smaller exciter-and-pickup coil of the at least two exciter-and-pickup coils, wherein said temperature and pressure sensors are located in a lower part of the case, under said larger exciter-and-pickup coil.

24. The defectoscope of claim 21, further comprising a smaller exciter-and-pickup coil of the at least two exciter-and-pickup coils, wherein said smaller and larger exciter-and-pickup coils and said magnetic field, pressure and temperature sensors are connected to said electronic module.

25. The defectoscope of claim 20, wherein said electronic module sends the second magnetization current pulses to a larger exciter-and-pickup coil of said coils and the first magnetization current pulse to a smaller exciter-and-pickup coil of said coils, and the electronic module is further configured to record and store responses of said exciter-and-pickup coils.

26. The defectoscope of claim 20, wherein said electronic module comprises a memory unit.

27. The defectoscope of claim 20, wherein said electronic module comprises a signal amplifier.

28. The defectoscope of claim 20, wherein the length of a smaller exciter-and-pickup coil of the at least two exciter-and-pickup coils is approximately 4/3 of the diameter of a first metal barrier, and the length of the larger exciter-and-pickup coil is approximately 4/3 of the diameter of a second metal barrier.

29. The defectoscope of claim 20, wherein the length of each successive coil in a series of coils is approximately 4/3 of the diameter of each successive metal barrier in a series of metal barriers.

30. The defectoscope of claim 20, wherein said defectoscope is configured to identify defects in the first metal barrier being a tubing metal barrier and the second metal barrier being a production casing metal barrier.

31. The defectoscope of claim 20, wherein the number of exciter-and-pickup coils is equal to the number of metal barriers under study.

32. The defectoscope of claim 20, wherein a smaller exciter-and-pickup coil of the at least two exciter-and-pickup coils is placed above the larger exciter-and-pickup coil.

33. The defectoscope of claim 20, wherein the distance between the coils does not exceed a length of the case.

34. The defectoscope of claim 20, wherein a smaller exciter-and-pickup coil of the at least two exciter-and-pickup coils and the larger exciter-and-pickup coil each contain an exciter winding wound around a pickup winding that, in turn, is wound around cores of said exciter-and-pickup coils.

35. The defectoscope of claim 20, wherein the case has a battery compartment located in an upper part of said case, and wherein the battery compartment is connected to said electronic module.

36. The defectoscope of claim 20, further comprising upper and lower centralizers, wherein said upper and lower centralizers are installed at a top and bottom of the case, respectively.

37. The defectoscope of claim 20, wherein cores of said exciter-and-pickup coils are made of soft ferromagnetic material.

38. The defectoscope of claim 20, wherein the case is made of titanium.

* * * * *